US00PP30529P2

(12) United States Plant Patent
Bruinen

(10) Patent No.: US PP30,529 P2
(45) Date of Patent: May 21, 2019

(54) ***ZAMIOCULCAS* PLANT NAMED 'EDZAMDARK1'**

(50) Latin Name: ***Zamioculcas zamiifolia* (hort. Lodd.) Engl.**
Varietal Denomination: EDZAMDARK1

(71) Applicant: EDPLANT B.V., Maasdijk (NL)

(72) Inventor: Ed Bruinen, Maasdijk (NL)

(73) Assignee: EDPLANT B.V., Maasdijk (NL)

( * ) Notice: Subject to any disclaimer, the term of this patent is extended or adjusted under 35 U.S.C. 154(b) by 0 days.

(21) Appl. No.: 15/932,046

(22) Filed: Jan. 25, 2018

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373
CPC ..... A01H 5/12
See application file for complete search history.

(56) References Cited

PUBLICATIONS

UPOVROM Plant Variety Database Citation for 'EDZAMDARK1' as per QZ PBR20142494; Dec. 15, 2014; 1 page.*

* cited by examiner

*Primary Examiner* — Kent L Bell
(74) *Attorney, Agent, or Firm* — Samuel R. McCoy, Jr.

(57) ABSTRACT

'EDZAMDARK1' is a new and distinctive variety of *Zamioculcas* plant which is characterized by a compact growth habit and an abundance of dark green foliage. The new variety propagates successfully by leaf cuttings and has shown to be uniform and stable in the resulting generations from asexual propagation.

2 Drawing Sheets

Latin name of the genus and species: The Latin name of the genus and species of the novel variety disclosed herein is *Zamioculcas zamiifolia* (hort. Lodd.) Engl.

Variety denomination: The inventive variety of *Zamioculcas* disclosed herein has been given the variety denomination 'EDZAMDARK1'.

BACKGROUND OF THE INVENTION

Parentage: 'EDZAMDARK1' is a naturally occurring whole-plant mutation of an unnamed *Zamioculcas zamiifolia* plant (not patented) which was discovered by the inventor in the summer of 2012 at a commercial greenhouse in Maasdijk, The Netherlands. The mutation was noted for its darker green foliage and compact growth habit.

Asexual Reproduction: Asexual reproduction of 'EDZAMDARK1' was first accomplished in the summer of 2012 by way of stem cuttings at a commercial greenhouse in Maasdijk, The Netherlands. Four successive generations produced from stem cuttings have shown that the unique features of the instant cultivar are stable and reproduce true to type.

SUMMARY OF THE INVENTION

The cultivar 'EDZAMDARK1' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new

*Zamioculcas* cultivar, 'EDZAMDARK1'. These traits, in combination, distinguish 'EDZAMDARK1' as a new and distinct cultivar.

1. *Zamioculcas* 'EDZAMDARK1' exhibits a compact growth habit; and
2. *Zamioculcas* 'EDZAMDARK1' exhibits an abundance of pinnately compound foliage, which arises directly from tuberous rhizomes; and
3. *Zamioculcas* 'EDZAMDARK1' exhibits foliage with dark green broad elliptic leaflets and dark green petioles.

BOTANICAL DESCRIPTION OF THE PLANT

Figure 1:
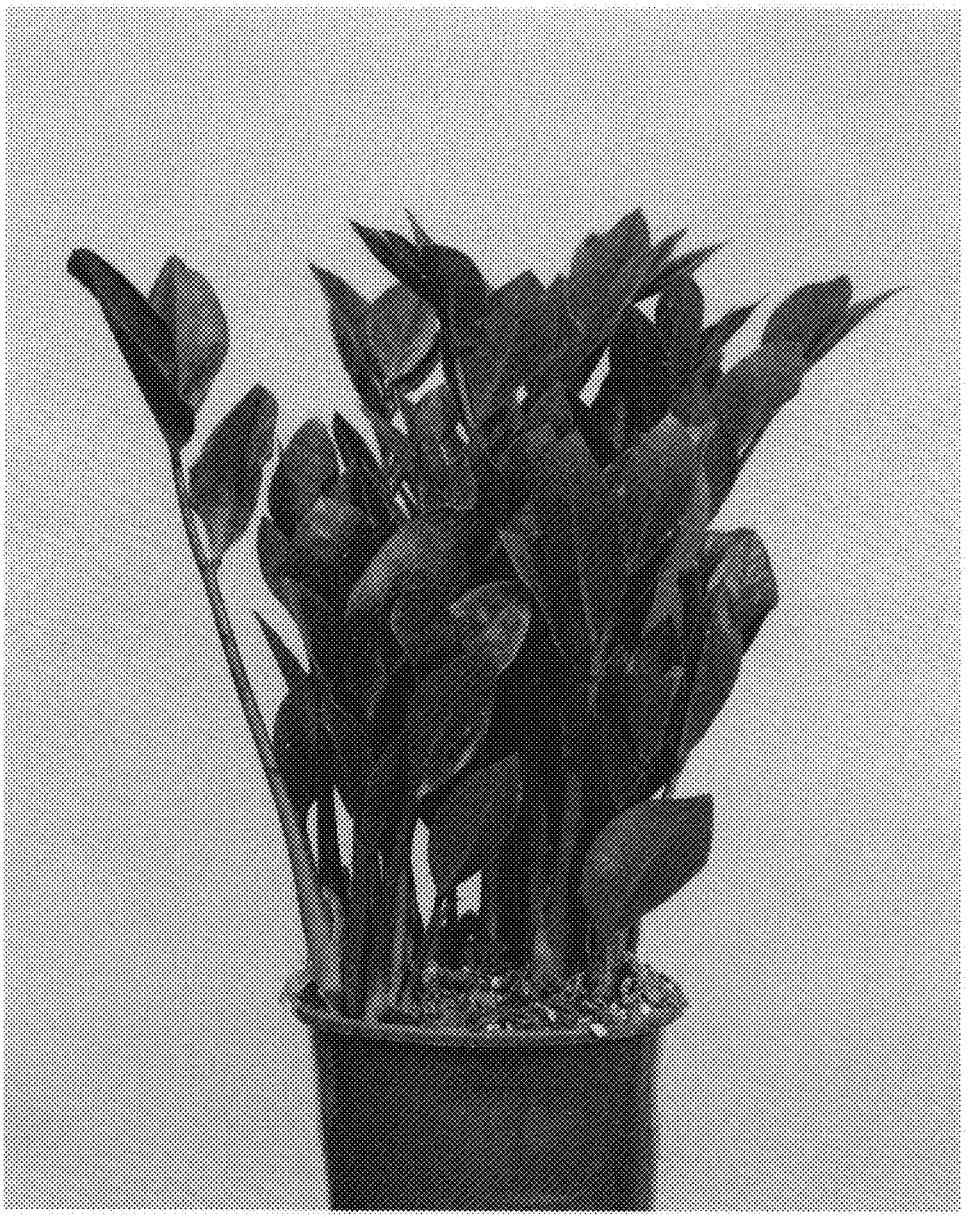
FIG. 1 shows, as nearly true as it is reasonably possible to make the same in color illustrations of this type, the typical foliage and growth characteristics of the new cultivar, 'EDZAMDARK1'. The plant shown is approximately 10 months old, potted into a 14 cm nursery pot, grown at a commercial greenhouse in Maasdijk, The Netherlands.
Figure 2:
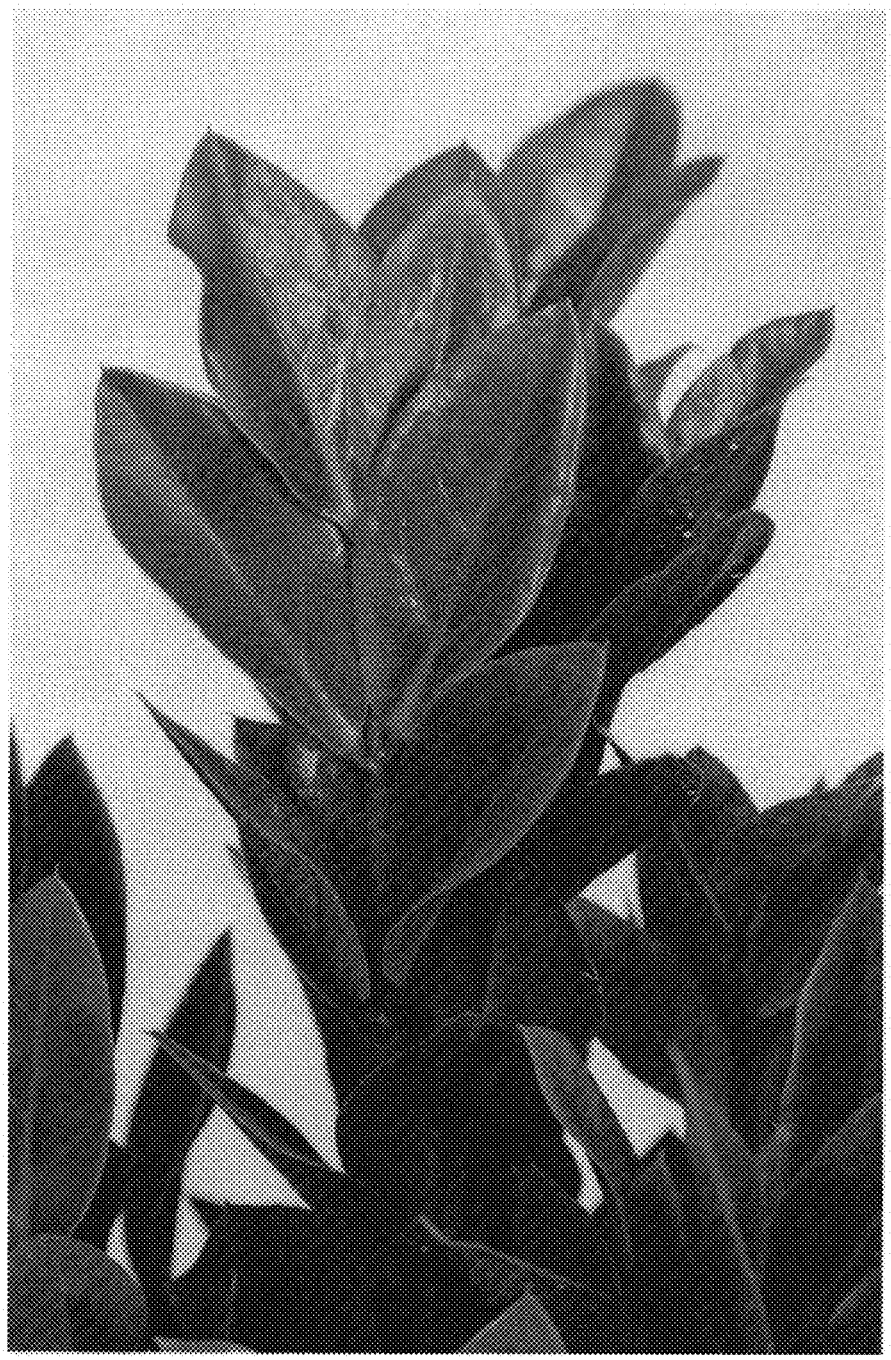
FIG. 2 shows, as nearly true as it is reasonably possible to make the same in color illustrations of this type, the typical foliage of the plant in FIG. 1.

The following is a detailed botanical description of a new and distinct variety of *Zamioculcas* hybrid known as 'EDZAMDARK1', based upon observations of 10 month old plants, potted into 14 cm nursery pots and grown indoors at a commercial nursery in Maasdijk, The Netherlands. Plants were grown in full sun using accepted fertility and irrigation practices for *Zamioculcas* plants. With the exception of preventative fungicides, no chemical pest control measures were employed. Furthermore, no artificial light or photoperiodic treatments were given to the plants. Observation data was recorded in November of 2017.

Those skilled in the art will appreciate that certain characteristics will vary with older or, conversely, with younger plants. 'EDZAMDARK1' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, sixth edition, 2015.

A botanical description of 'EDZAMDARK1' and comparisons with the parent plant and the most similar variety of common knowledge are provided below.

General plant description:

*Growth habit.*—Tropical evergreen perennial.

*Plant form.*—Broad oblong; compact.

*Growth rate.*—Low to moderate.

*Plant vigor.*—Moderate.

*Height.*—27.6 cm to the top of the foliar plane.

*Width.*—30.0 cm.

*Propagation.*—Type — Leaf cuttings. Time to initiate rooting — Approximately 30 days at an approximate temperature of 25 degrees Celsius. Crop time — Approximately 1 year to produce a marketable plant in a 12 cm container; 1.5 years to produce a marketable 17 cm container.

*Pathogen and pest resistance and susceptibility.*—Plants have not been observed to be susceptible or resistant to pathogens and pests common to *Zamioculcas* sp.

*Environmental tolerances.*—Adapt to, at least, USDA Zones 10 to 12 and temperatures ranging from 5 to 40 degrees Celsius; moderate tolerance to rain; low tolerance to wind.

Stem:

*Branching habit.*—No stems or branches; compound leaves in small clumps, arising directly from tuberous rhizomes.

*Number of clumps per plant.*—Five, on average.

*Number of additional clumps formed each year.*—Three, on average.

Root system:

*Type.*—Tuberous rhizomes bearing thick fleshy roots.

*Shape of rhizomes.*—Irregular oblong to ovoid.

*Dimensions of rhizomes.*—6.4 cm long and 4.4 cm in diameter.

*Density of rhizomes and roots.*—Moderately dense.

*Distribution of rhizomes and roots.*—Rhizomes shallow; roots distributed evenly throughout the soil profile, from shallow to deep.

*Texture of rhizomes and roots.*—Glabrous and very fleshy.

*Color of rhizomes and roots.*—Greyed-brown, nearest to in between RHS 199B and N199A.

Foliage:

*Arrangement.*—Compound leaves in small clumps, arising directly from tuberous rhizomes.

*Attachment.*—Petiolate.

*Division.*—Pinnately compound.

*Dimensions.*—26.0 cm long and 10.0 cm wide.

*Stipules.*—General — Two papery stipules present at the base of each pinnately compound leaf. Shape — Ovate. Length — 5.8 cm. Width — 3.3 cm. Apex — Acute. Base — Cuneate. Margin — Entire, moderately undulated. Texture — Papery. Color, adaxial and abaxial surfaces — Nearest to a combination of greyed- orange, RHS 165A, and brown, RHS 200D.

*Petiole.*—Appearance; cross-section — Rounded. Length — 20.4 cm. Diameter — 1.1 cm at the base and 0.5 cm on average. Attitude — Approximately 5 degrees from vertical. Strength — Strong and flexible. Color, juvenile — Yellow-green, nearest to RHS 148A but slightly darker. Color, mature — Yellow-green, nearest to RHS 148A. Color at the internodes — Nearest to in between yellow-green, RHS 147A, and greyed-green, RHS 197A. Texture — Glabrous. Luster — Moderately glossy.

*Leaflets.*—Quantity — 6 to 8 pairs of opposite leaflets. Attitude — Upright. Dimensions — 7.5 cm long and 3.4 cm wide. Shape — Elliptic. Aspect — Slightly carinate. Apex — Narrow abruptly acute. Base — Attenuate. Margin — Entire; slightly undulated. Texture, adaxial surface — Slightly coriaceous. Texture, abaxial surface — Slightly coriaceous. Luster, adaxial surface — Glossy. Luster, abaxial surface — Glossy. Color — Juvenile foliage color, adaxial surface — Green, nearest to in between RHS 141A and 143A. Juvenile foliage color, abaxial surface — Nearest to in between green, RHS 143A, and yellow-green, RHS 144A. Mature leaf color, adaxial surface — Nearest to in between green, RHS 139A, and yellow-green, RHS N147A. Mature leaf color, abaxial surface — Green, nearest to in between RHS 137A and 143A but darker. Venation — Pattern — Pinnate. Vein color, adaxial surface — Green, nearest to a combination of RHS 143A and 143B. Vein color, abaxial surface — Green, nearest to RHS 143B. Petiolule — Length — 0.5 cm. Diameter — Petioles flattened; average width is 0.4 cm and the average height is 0.3 cm. Strength — Strong. Color, adaxial surface — Yellow-green, nearest to RHS 147A but slightly darker. Color, abaxial surface — Yellow-green, nearest to RHS 147A. Texture, adaxial and abaxial surfaces — Glabrous. Luster, adaxial and abaxial surfaces — Slightly glossy.

Inflorescence: No flowering has been observed to date.

Comparison with the parent plant: Plants of the new cultivar 'EDZAMDARK1' may be distinguished from its parent, an unnamed *Zamioculcas zamiifolia* plant, by the characteristics described in Table 1.

TABLE 1

Comparison Between 'EDZAMDARK1' and The Parent

| Characteristic | 'EDZAMDARK1' | The parent |
|---|---|---|
| Growth habit. | More clumps of foliage per plant; plants are more compact. | Fewer clumps of foliage per plant; plants are less compact. |
| General coloration of the petioles. | Darker green, especially in juvenile foliage. | Lighter green. |
| Leaflet shape. | Elliptic but broader than the parent; closer to ovate. | Elliptic but more narrow than 'EDZAMDARK1'. |

TABLE 1-continued

| Comparison Between 'EDZAMDARK1' and The Parent | | |
|---|---|---|
| Characteristic | 'EDZAMDARK1' | The parent |
| Leaflet size. | Slightly smaller than the parent. | Slightly larger than 'EDZAMDARK1'. |
| General coloration of the foliage. | Darker green. | Lighter green. |

Comparisons with the most similar variety of common knowledge: Plants of the new cultivar 'EDZAMDARK1' are most similar to the commercial variety, *Zamioculcas* 'EDZAMVIG1' (Community Plant Variety Rights grant number 45882). A comparison of 'EDZAMDARK1' with 'EDZAMVIG1' is described in Table 2.

TABLE 2

| Comparison Between 'EDZAMDARK1' and 'EDZAMVIG1' | | |
|---|---|---|
| Characteristic | 'EDZAMDARK1' | 'EDZAMVIG1' |
| Growth habit. | More clumps of foliage per plant; plants are more compact. | Fewer clumps of foliage per plant; plants are less compact. |
| Abundance of foliage. | More abundant. | Less abundant. |
| General coloration of the foliage. | Darker green. | Lighter green. |

That which is claimed is:

1. A new and distinct variety of *Zamioculcas* plant named 'EDZAMDARK1', substantially as described and illustrated herein.

* * * * *